(12) United States Patent
Horstmann et al.

(10) Patent No.: US 10,471,021 B2
(45) Date of Patent: Nov. 12, 2019

(54) TRANSDERMAL THERAPEUTIC SYSTEM FOR THE ADMINISTRATION OF PEPTIDES

(71) Applicant: LTS Lohmann Therapie-Systeme AG, Andernach (DE)

(72) Inventors: Michael Horstmann, Neuwied (DE); Gerd Hoffmann, Neuwied (DE); Sandra Wiedersberg, Steigra (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 0 days.

(21) Appl. No.: 15/867,050

(22) Filed: Jan. 10, 2018

(65) Prior Publication Data

US 2018/0133165 A1 May 17, 2018

Related U.S. Application Data

(62) Division of application No. 13/512,520, filed as application No. PCT/EP2010/007323 on Dec. 2, 2010, now Pat. No. 9,895,319.

(30) Foreign Application Priority Data

Dec. 4, 2009 (DE) .................. 10 2009 056 745

(51) Int. Cl.
*A61K 9/70* (2006.01)
*A61K 38/24* (2006.01)
*A61K 38/27* (2006.01)
*A61P 5/06* (2006.01)

(52) U.S. Cl.
CPC ............ *A61K 9/7084* (2013.01); *A61K 38/24* (2013.01); *A61K 38/27* (2013.01); *A61P 5/06* (2018.01)

(58) Field of Classification Search
CPC ..... A61M 37/00; A61M 35/00; A61K 9/7084; A61K 38/24; A61K 38/27; A61P 5/06
See application file for complete search history.

(56) References Cited

U.S. PATENT DOCUMENTS

| 4,573,996 | A | * | 3/1986 | Kwiatek | A61K 9/7084 424/434 |
| 4,675,009 | A | * | 6/1987 | Hymes | A61B 5/04087 424/448 |
| 4,699,146 | A | * | 10/1987 | Sieverding | A61L 15/58 600/391 |
| 4,710,191 | A | * | 12/1987 | Kwiatek | A61K 9/7084 424/449 |
| 4,784,857 | A | * | 11/1988 | Berry | A61K 9/7084 424/443 |

(Continued)

FOREIGN PATENT DOCUMENTS

| DE | 20 2006 000662 U1 | 3/2006 |
| DE | 10 2007 006244 A1 | 8/2008 |

(Continued)

*Primary Examiner* — Theodore J Stigell
(74) *Attorney, Agent, or Firm* — ProPat, L.L.C.

(57) ABSTRACT

The invention relates to a transdermal therapeutic system (TTS), which is suited for the administration of a peptide to a patient through skin treated with ablation. The transdermal therapeutic system includes a back layer and an active substance-containing layer that contains at least one peptide and a carrier substance, preferably as a textile web material.

20 Claims, 2 Drawing Sheets

(56) References Cited

U.S. PATENT DOCUMENTS

| | | | | |
|---|---|---|---|---|
| 4,818,540 A * | 4/1989 | Chien | | A61K 9/7069 424/448 |
| 4,906,169 A * | 3/1990 | Chien | | A61K 9/7061 424/447 |
| 5,023,084 A * | 6/1991 | Chien | | A23G 1/56 424/448 |
| 5,338,490 A * | 8/1994 | Dietz | | A61B 5/04087 252/500 |
| 5,391,375 A * | 2/1995 | Hille | | A61K 9/703 424/448 |
| 5,503,844 A * | 4/1996 | Kwiatek | | A61K 9/703 424/434 |
| 5,529,784 A * | 6/1996 | DiPippo | | A61F 13/00063 424/195.18 |
| 6,011,011 A * | 1/2000 | Hageman | | A61K 9/0014 424/438 |
| 6,264,979 B1 * | 7/2001 | Svedman | | A61K 9/7084 424/447 |
| 7,446,090 B2 * | 11/2008 | Hoffmann | | A61K 9/0019 514/1.1 |
| 2002/0038101 A1 * | 3/2002 | Avrahami | | A61N 1/30 604/20 |
| 2003/0147943 A1 | 8/2003 | Luo et al. | | |
| 2004/0033254 A1 * | 2/2004 | Song | | A61K 9/7053 424/449 |
| 2005/0163827 A1 * | 7/2005 | Zech | | A61K 9/703 424/448 |
| 2006/0034904 A1 * | 2/2006 | Weimann | | A61K 9/0009 424/449 |
| 2007/0190123 A1 * | 8/2007 | Aida | | A61K 9/7084 424/448 |
| 2009/0170757 A1 * | 7/2009 | Fraser | | A61K 31/395 514/1.1 |

FOREIGN PATENT DOCUMENTS

| | | |
|---|---|---|
| JP | 2004-520152 A | 7/2004 |
| JP | 2004-538345 A | 12/2004 |
| WO | WO 95/30410 A2 | 11/1995 |
| WO | WO 2001/80859 A1 | 11/2001 |
| WO | WO 2004/039426 A2 | 5/2004 |
| WO | WO 2005/042054 A2 | 5/2005 |
| WO | WO 2007/039646 A1 | 4/2007 |
| WO | WO 2008/095597 A2 | 8/2008 |

* cited by examiner

Figure 3: Transdermal therapeutic system:

Figure 4: FSH permeation profile, in vitro permeation:

TRANSDERMAL THERAPEUTIC SYSTEM FOR THE ADMINISTRATION OF PEPTIDES

CROSS-REFERENCE TO RELATED APPLICATIONS

This application is being filed as a divisional application of and claims priority to U.S. patent application Ser. No. 13/512,520, filed May 29, 2012, which has matured into U.S. Pat. No. 9,895,319, claiming priority to National Stage Application of International Application No. PCT/EP2010/007323 filed Dec. 2, 2010, which further claims priority to German Patent Application No. 10 2009 056 745.3, filed Dec. 4, 2009. Each of U.S. patent application Ser. No. 13/512,520; International Application No. PCT/EP2010/007323 and German Patent Application No. 10 2009 056 745.3 are hereby incorporated by reference herein in their entirety.

FIELD OF THE INVENTION

The subject matter of the present invention is a transdermal therapeutic system (ITS) for administering peptides and other molecules of high molecular weight. Particularly suitable in this respect are those peptides which can be used as active pharmaceutical ingredients. These include, in particular, the peptide hormones, especially FSH.

BACKGROUND OF THE INVENTION

Transdermal therapeutic systems (ITS) as pharmaceutical administration forms have been known for a long time. For the transdermal administration of active pharmaceutical ingredients by means of TTS, the stratum corneum (SC), the outermost layer of the skin, in the majority of cases constitutes the real barrier for the permeability and for the rate of passage of the active pharmaceutical ingredient.

Peptides and proteins and also other high-molecular molecules, with a molecular weight of more than 500 daltons—such as, for example, tacrolimus, heparin, and numerous salts of betamethasone—are generally not absorbed transdermally, owing to their molecular size and to their physicochemical properties.

Moreover, the majority of peptides possess a low oral bioavailability and are subject to severe, proteolytic degradation in the gastrointestinal tract. For these reasons, peptides are commonly administered parenterally, bypassing the gastrointestinal tract. This involves injections or infusions which are administered below the skin, into the muscle or directly into the bloodstream.

The transdermal route here would offer a noninvasive alternative—with high patient compliance—to this invasive, parenteral administration. Consequently there are numerous approaches to facilitating the permeability of the skin for molecules having a molecular weight of more than 500 daltons. These approaches include, primarily, the use of permeation enhancers or the additional use of heat.

Another technique for making molecules with poor skin transit amenable to transdermal administration is to facilitate the passage of an active ingredient of this kind through the stratum corneum by partly destroying or removing this layer beforehand. These techniques, referred to as "skin ablation", use thermal or mechanical energy in order to effect partial destruction or removal of the stratum corneum and hence to create direct channels into the living epidermis. The permeability of the skin is increased and the transdermal absorption of high-molecular-weight molecules can therefore be made possible.

As a result of this pretreatment of the skin, moreover, it is also possible for hydrophilic active ingredients to be administered transdermally, the transdermal route having hitherto been closed to such ingredients on account of their hydrophilicity. Ingredients contemplated here include, for example, fentanyl citrate, granisetrone HCl, Na diclofenac, and apomorphine sulfate. Furthermore, the TTS area of existing TTS systems can be reduced significantly, for the same blood levels, by means of skin ablation pretreatment.

The skin ablation technique commonly generates a multiplicity of microchannels through the stratum corneum, and yet the percentage "perforated" proportion of the treated skin area is relatively small. A description of the laser skin ablation technique is present in WO 2007/039646, whose equivalent is United States Patent Publication No. 2008/0255034 A1.

Follicle-stimulating hormone (FSH, follitropin) is a gonadotropic hormone of the anterior lobe of the hypophysis, and is also called follicle maturation hormone, gonadotropin A, prolan A or thylakentrin. Human FSH is an acidic glycoprotein (isoelectric point 4.5) with a 16% carbohydrate fraction and a molecular weight of around 34 000 daltons. Its α-polypeptide chain (with 92 amino acid residues) is virtually identical with that of chorio(nic)gonadotrop(h)in. The β-chain, which is specific for FSH, contains 111 amino acid residues. FSH promotes growth and development of the gonads and incites them to hormone synthesis. In women, it plays a part in the menstrual cycle, by causing a new follicle to mature, and to produce estradiol. In the human gonads, it stimulates the formation of spermatogenic cells. For the use described here, it is possible to use FSH from natural sources or recombinant FSH.

FSH has a relatively short half-life. In the context of the superovulation of ruminants, hypophyseal extracts have been much used, and then, however, may contain not only FSH but also varying amounts of LH (luteinizing hormone). Today, recombinant FSH products are also available commercially (GONAL F®, PUREGON®).

Somatropin (also: somatotropic hormone, STH, GH) is a species-specific hormone which is formed in the anterior lobe of the hypophysis and is responsible for the growth process. The human growth hormone, also called HGH (hypophyseal or human growth hormone), is an individual polypeptide, with a molar mass of about 21 500, composed of 191 amino acids with 2 disulfide bridges. In terms of its composition, human somatotropin is closely related to placental lactogen and also to prolactin. In liver and kidney, somatotropin causes the excretion of insulinlike growth factors which are responsible for much of the effects of somatropin. Somatotropin secretion is inhibited by somatostatin, and stimulated by the releasing hormone somatoliberin (SRF or SRH or GH-RF or GR-RH) from the hypothalamus.

Dwarfism caused in children by the absence or underproduction of somatotropin can be regulated by supply of human growth hormone, which has since been produced recombinantly in the USA as PROTROPIN® (Genentech) and—with a different amino acid residue—HUMATROPE® (Eli Lilly). Other medical applications for somatotropin, might arise in the case of burns, signs of aging, osteoporosis, cardiovascular disorders, and obesity.

The known products, however, possess certain disadvantages, which are attributable in particular to the low stability of the peptides in solution, this low stability being common knowledge.

Molecules of high molecular weight have to date been closed off from transdermal administration as a result of their physicochemical properties. Transdermal administration of these molecules is made possible only by pretreatment of the skin.

Lastly, injection itself may toe accompanied by difficulties, which lie primarily in pain during application, a risk of injury, and the risk of infections.

SUMMARY OF ADVANTAGEOUS EMBODIMENTS OF THE INVENTION

It is an object of the present invention to provide a transdermal therapeutic system (TTS) for the administration of peptides and other molecules with poor skin access.

In order for the TTS to be stable on storage at room temperature and to have little susceptibility to microbes, it ought to include as little water as possible.

The TTS here is to be applied to an area of skin of which beforehand at least a subregion of the stratum corneum has been destroyed, or removed.

The intention in particular is to manufacture a TTS with the active ingredient follitropin (FSH; follicle-stimulating hormone) and/or one of its pharmaceutically acceptable salts, with which this peptide can be administered through the skin in therapeutic doses to a patient.

The skin is preferably to be skin which has undergone an "ablative" pretreatment, where a proportion of the stratum corneum has been removed.

The intention here is not only to avoid the route of administration by injection. The TTS itself is as far as possible, to be equipped without microinjection needles, microblades and/or other needles and barbs, in order to avoid or rule out additional mechanical injury to the stratum corneum. However, where appropriate, the TTS may also be furnished with construction elements of these kinds.

It is also the intention that the peptide can be applied by means of the transdermal therapeutic system as part of a long-term application.

The product, is also to be amenable to production in a simple and cost-effective way.

DETAILED DESCRIPTION OF ADVANTAGEOUS EMBODIMENTS OF THE INVENTION

The object is achieved by means of a transdermal therapeutic system (ITS) for administering peptides, which comprises an active ingredient layer which comprises a peptide and a preferably hydrophilic carrier substance for the peptide.

The TTS may further comprise a backing layer which is impermeable to the peptide. In one preferred embodiment the backing layer is coated on the side facing the active ingredient layer with a water-insoluble, pressure-sensitively adhesive polymer. A backing layer of this kind preferably possesses an area which is greater than the area of the active ingredient layer. In such a TTS, the backing layer forms an "overpatch" which ensures the reliable adhesion of the TTS on the skin.

The active ingredient layer may comprise further excipients which stabilize the active ingredient, preferably buffer substances or sugars, but also stabilizers and preservatives.

The TTS may also comprise at least one further, additional layer of pressure-sensitive adhesive, which is substantially free from active ingredient and is pressure-sensitively adhesive. An additional layer of pressure-sensitive adhesive of this kind ensures reliable adhesion of the TTS on the skin in the event that the active ingredient layer is not, or not sufficiently, pressure-sensitively adhesive.

The TTS may comprise active peptidic ingredients, more particularly peptides having a molecular weight of greater than 1 500 Da.

In one particular embodiment, the TTS comprises the active ingredient follitropin and/or at least one of its pharmaceutically acceptable salts.

In another particular embodiment, the TTS comprises the active ingredient somatotropin.

A "transdermal therapeutic system" (TTS) is a product of laminar construction. In its simplest embodiment it consists of a backing layer, an active ingredient layer, and a protective sheet which lines the active ingredient layer before the TTS is employed. In this kind of simple construction, the active ingredient layer is preferably made pressure-sensitively adhesive. If, however, the bond strength of the active ingredient layer is not sufficient, the TTS may feature an additional layer of pressure-sensitive adhesive.

This additional layer of pressure-sensitive adhesive may be disposed between the active ingredient layer and the protective sheet.

In one preferred embodiment, the additional layer of pressure-sensitive adhesive is sited between the active ingredient layer and the backing layer. In this case, in at least one section along the side margin/margins of the active ingredient layer, the layer of pressure-sensitive adhesive protrudes beyond the active ingredient layer.

The additional layer of pressure-sensitive adhesive then acts as an "overpatch" during the application of the TTS, ensuring reliable adhesion to the skin.

The TTS may also possess a membrane which controls the rate of emergence of the active ingredient from the active ingredient layer. The membrane is therefore sited on the side of the active ingredient layer that is facing the skin during the application of the TTS.

The TTS itself may, finally, possess a needle layer, which comes directly into contact with the skin and is furnished on its bottom face with microinjection needles (i.e., hollow needles for the flow passage of active, ingredient), microblades (for scoring the uppermost layers of skin), needles (for perforating the uppermost layers of skin) and/or barbs (for anchoring in the skin). In one preferred embodiment, however, the TTS is furnished without such a layer.

In another embodiment, the transdermal therapeutic system may comprise, more than one active ingredient layer. These active ingredient layers may be disposed one above another (forming an at least two-layer laminate) or next to one another. In the case of a TTS of this kind having more than one active ingredient layer, the individual layers may have the same construction or different constructions. In "multilayer systems" of these kinds, however, these layers differ preferably on the basis of their composition or of the active ingredient used.

The active ingredient layer may also be present in the form of a liquid-filled pouch or liquid-filled chamber, in which the active ingredient is present in dissolved, dispersed or suspended form.

Finally, the active ingredient in the active ingredient layer may be present in liquid microresevoirs, which are in dispersion in the active ingredient layer.

With the TTS described here it is possible with preference to administer active peptide ingredients by the transdermal route. The technical teaching, however, can in principle also be utilized for other physiologically active substances, including more particularly those which have been hitherto unavailable for transdermal therapy (hydrophilic active ingredients) or possess a molecular mass of more than 500, preferably more than 1500 daltons.

"Peptides", for the purposes of the present description are amino acid condensation products that are linked in acid amide fashion by peptide bonds. Where the molecules are constructed from two amino acid residues, they are also referred to as dipeptides; in the case of three or more, as tripeptides, tetra-, pentapeptides etc. Peptides having 2-10 amino acid residues are therefore generally referred to collectively as oligopeptides, those with 10-100 as polypeptides. The transition from the latter to the higher-molecular-weight proteins is, however, not precisely defined. Peptides having bonds between the pendant amino groups of diaminocarboxylic acids and pendant carboxyl groups of aminodicarboxylic acids instead of the customary peptide bonds between the α-amino group and the carboxyl group are called isopeptides; the additional bonds originating from polyfunctional amino acids such as glutamic acid, aspartic acid, lysine, and arginine are responsible for the formation of peptide network structures.

The preferred peptides include peptide hormones. These are peptides of high physiological activity which develop hormone or hormonelike effects. Generally speaking, the peptide hormones are oligopeptides and polypeptides (having up to 100 amino acids), but occasionally are also higher-molecular-weight proteins (proteohormones). These include the glandular peptide hormones of the hypophysis (e.g.; corticotrophin follitropin, lutropin, melanotropin, prolactin, somatotropin, thyrotropin, oxytocin, vasopressin), the releasing hormones and inhibiting factors of the hypothalamus, the peptide hormones from pancreas, stomach or gut (e.g.: glucagon, insulin, somatostatin, secretin, gastrin, cholecysto-kinin), from the thyroid gland (e.g. $^H$calcitonin, parathyrin). Certain oligopeptides have not only a conventional hormone activity but also growth factor activity, neurotransmitter activity or neuromodulator activity (mediators). Examples of such include the endogenous opiates, enkephalins and endorphins.

The peptides can be used preferably in the form of a pharmaceutically acceptable salt.

Classed among the peptides in the sense of this description are not only natural peptides and peptide hormones but also nature-identical and/or modified (that is, produced synthetically) peptides and peptide hormones, conjugated proteins (i.e., glycopeptides and glycoproteins, lipoproteins, metalloproteins, and others.

"Skin" means the normal, intact skin of a human being or mammal. The skin has a layered construction and consists—as seen from outside to inside—of epidermis, dermis, and subcutis. Within these three components, the skilled person may distinguish further layers.

In the case of the epidermis, five layers are distinguished; the horny layer (stratum corneum), shiny-layer (stratum lucidum), granular layer (stratum granulosum), spiny cell layer (stratum spinosum), and basal layer (stratum basale).

"Ablatively treated skin" means the normal, intact skin of a human being of whose epidermis the stratum corneum has—at least partly—been destroyed or removed. In this area of ablatively treated skin, the "proportional area of normal, intact skin of whose epidermis the at least the stratum corneum has been destroyed or removed" (corresponding to the sum of the areas X in FIG. 2) relative to the "total normal, intact skin on whose epidermis the stratum corneum remains" (corresponding to the area A in FIG. 2) may be below 50%, preferably below 20%, and more preferably below 10%. The sections of the epidermis at which the stratum corneum has been removed may be irregular in shape. Preferably, however, they are of defined shape and area. Suitable shapes contemplated include rectangles, hexagons, octagons, squares, circles, and spots. The sections of the epidermis which are removed by ablative treatment have a depth such that at least the stratum corneum is removed at the locations in question and so the "microchannels" are formed beneath the areas X (cf. FIG. 2). The sections of the epidermis removed by ablative treatment are preferably, however, not to extend any deeper than down to the dermis. This can be achieved by means of corresponding adaptation of the laser power and simultaneous check measurements.

The term "transdermal" refers to the route of administration through the skin of a human, being or mammal. Skin here means both the normal, intact skin and also the "ablatively treated skin" in the sense of the above definition.

Substances contemplated as the "carrier substance" for the active ingredient layer include substances which behave compatibly in relation to the at least one peptide. It is known that, with peptides, not only chemical influences, such as, for example, acids, salts or organic solvents, but also physical exposures, such as high or low temperatures or else pressure, may alter the secondary and tertiary structure and hence ultimately, also the quaternary structure (denaturing). Denaturing may also cause changes in the physical and physiological properties of the peptides. In the case of chemical cleavage of the peptides (proteolysis), fragments are produced from them, and are called peptones.

As far as the requirements concerning the compatibility of the carrier substance are concerned, this means that, when the peptide is imbedded into the carrier substance, there must foe no interaction with the peptide that lead to any such change in the structure of the peptide or to any deterioration otherwise originating of its pharmacological properties.

The effect of the carrier substance is that the at least one peptide is distributed uniformly in the active ingredient layer. The carrier substance preferably has the effect that the peptide molecules are present individually, i.e., in the form of a true "solution".

It has emerged that suitable carrier substances are more particularly those which are "hydrophilic". By hydrophilic ("water-loving") is meant the capacity to bind water or to penetrate water and, in a further sense, "to be wetted effectively by water".

The carrier substance may be present in the active ingredient layer in the form of fibers, powder or a film. The carrier substance preferably forms a film having a constant layer thickness. This layer thickness may be between 20 and 200 µm, preferably between 30 and 80 µm.

In another preferred embodiment, the carrier substance takes the form of a sheetlike textile structure, preferably as a nonwoven composed of individual fibers, or else in the form of a woven or knitted fabric of yarn. In these cases the carrier substance is not water-soluble.

The active ingredient layer may comprise "buffers" in order to maintain a defined pH therein and to increase the stability of the active ingredient. Buffer systems and the pH values which can be set using them are known to the skilled person. For FSH, a buffer which ensures a pH of approximately 7 is preferred.

Layers contemplated as the "backing layer" are occlusive and nonocclusive layers, with the occlusive layers being preferred. These layers are constructed of films/foils, woven and/or knitted fabrics, with films/foils being preferred. The materials involved are natural or synthetic polymers and metals. Particularly preferred are composite materials comprising synthetic polymers and metals in the form of laminates. The backing layer is preferably flexible and impervious for the active ingredient.

The "active ingredient layer" comprises—as already stated—at least one peptide and at least one carrier substance for the peptide. It may have an area of 1 to 100 $cm^2$, preferably of 2 to 80 $cm^2$, and more preferably between 4 to 20 $cm^2$. The thickness of the active ingredient layer may be between 10 and 200 µm, preferably between 15 and 90 µm, more preferably between 20 and 80 µm.

The "concentration" of the at least one peptide in the active ingredient layer is heavily dependent on the therapeutic indication, on the activity of the peptide in question, and on its molecular weight. The concentration may therefore vary within wide ranges and in the active ingredient layer may be between 0.1 to 99% by weight, preferably between 30 and 70% by weight.

In order for the active ingredient layer which comprises a peptide and a carrier substance for the peptide to be furnished "pressure-sensitively adhesively", it may be admixed with at least one "pressure-sensitive adhesive". The pressure-sensitive adhesives that are suitable are set out later on below. Another possibility involves furnishing the active ingredient layer pressure-sensitively adhesively by addition of plasticizers, tackifiers, etc. Especially when the carrier substance is highly hydrophilic, it is advantageous to use hydrophilic tackifiers such as pantothenyl alcohol, honey, low-molecular-weight carbohydrates (such as sucrose, glucose, fructose) and derivatives thereof (such as sucrose acetate isobutyrate, for example), and combinations thereof.

In one particular embodiment the active ingredient layer may comprise water. The water content (residual moisture content), however, is preferably low, in order not to jeopardize the mechanical stability of the active ingredient layer and to minimize other risks—more particularly microbiological risks—due to the presence of water. The "water content" in the active ingredient layer is preferably below 20%, more preferably below 10%, and very preferably below 5%.

The additional "pressure-sensitively adhesive layer" may be constructed from the "pressure-sensitive adhesives" that are known to the skilled person. Pressure-sensitive adhesives are able to induce "wetting", producing sufficient forces of adhesion, at room temperature, without, activation by solvent, or heat, solely by being pressed onto the surface of the article which is to be stuck.

As "pressure-sensitive adhesives" it is possible to use "polymers" which by virtue of the composition of their monomers possess pressure-sensitively adhesive properties. These include synthetic rubber and natural rubber, butyl rubber, styrene-butadiene copolymers, ethylene-vinyl acetate copolymers, acrylonitrile copolymers, polychloroprene, polyisobutylene, polyvinyl ethers, styrene-butadiene-styrene block polymers, styrene-isoprene-styrene block, polymers, polyacrylates, polyesters, polyurethanes, and polysiloxanes. The adhesive properties of the polymer obtained in the polymerization can be modified by functional groups in the monomers of these polymers. The polymers are water-insoluble.

Another way of modifying the adhesive properties of these stated polymers is afforded by the adaptation of the adhesive formula to the desired properties through addition of additives such as resins, plasticizers, tackifiers, fillers and/or stabilizers.

Particularly suitable polymers having pressure-sensitively adhesive properties are polyacrylates, polyisobutylenes, silicones, It is preferred to use those pressure-sensitive adhesives which are notable for their high physical compatibility with the peptides and which at the same time do not trigger any instances of skin irritation, allergies or sensitization in use.

As the "protective sheet" in the transdermal therapeutic system it is possible to use the films that are known to the skilled person, such as siliconized polyester films, for example.

The use of the transdermal therapeutic system (TTS) which comprises an active ingredient layer and at least one peptide and at least one carrier substance for the peptide is a further solution provided by the invention.

For this purpose, prior to the application of the TTS, the horny layer (the stratum corneum) of the skin is at least sectionally removed, preferably by means of the laser skin ablation technique. In one preferred embodiment this ablatively treated skin has microchannels in this area within the stratum corneum.

Subsequent application of the TTS allows transdermal absorption of the peptide. For this purpose, the TTS is placed directly onto the ablatively treated skin. The active ingredient layer, comprising the peptide and a carrier substance for the peptide, comes to lie directly above the ablatively treated skin in this case.

Owing to the at least local removal of the stratum corneum, the peptide is able to reach the underlying layers of the skin and ultimately to enter the circulation transdermally. Moisture originating from the layers of the skin below the Stratum corneum may facilitate the transport of the peptide through the at least locally removed sections of the stratum corneum (i.e., through the microchannels).

The additional pressure-sensitively adhesive layer may optionally be used to effect additional fixing of the TTS on the skin.

In one particular embodiment, during the application of the "skin ablation technique", the ablatively treated skin area is marked in color, allowing the subsequent application of the TTS to be performed with precision and ease.

The application time of one application may be from a few hours (for example, 2 to 6 hours) through to one or more (for example, 3 to 7) days. Repeated applications are possible as well. For this purpose, the TTS may be placed onto the ablatively treated skin on which a TTS has already been applied. Preferably the TTS—especially in the case of a relatively long-lasting therapeutic application—is always placed on an area of skin treated ablatively immediately beforehand.

One particular embodiment of the invention envisages using a transdermal therapeutic system (TTS) which comprises a backing layer which is furnished with a pressure-sensitively adhesive layer, a layer comprising FSH, a carrier substance in the form of a textile sheetlike structure, and a protective sheet as part of a fertility therapy.

For this purpose, in a first step, first of all the skin of a female patient is ablatively treated by a laser skin ablation technique. Then, in a second step, a TTS with a GnRH agonist (for example, leuprolide, buserelin, nafarelin, histrelin, goserelin or deslorelin, but preferably triptorelins) is applied to the skin location thus treated and is left on this skin location for a relatively long time period (at least 12 hours, preferably 24 to 48 hours). The GnRH agonist which is released in this operation is delivered transdermally to the patient, and results in a lowering of the endogenous FSH level in this patient, which is preferably measured regularly during the treatment. If the FSH level is still above the target value (which in general is below 10 mIU/ml), these first two steps are repeated, but on a different skin location.

If the measured level is below the target value for the endogenous FSH level in the patient, then, in the third step, a further skin location on the patient is treated ablatively by a laser skin ablation technique. Then in the fourth step, at this location, the TTS of the invention with the peptide FSH is applied. The transdermal administration of FSH produces an increase in the FSH level in the patient, and the formation of follicles, and this can be monitored preferably by ultrasound investigations. In concluding steps of the method, these follicles are removed, fertilized in vitro, and used for (e.g. transferred or implanted into) the patient or a "surrogate mother".

The method for producing a transdermal therapeutic system (TTS) for administering peptides, comprising an active ingredient layer which comprises at least one peptide and at least one carrier substance for the peptide, comprises a plurality of steps.

In the first step, the peptide is dissolved in water, preferably in a corresponding buffer. Particularly suitable solvents contemplated include isotonic saline solution and aqueous buffer solutions having a corresponding pH.

Other auxiliaries may be added to this active ingredient solution, such as, for example, stabilizers and preservatives (examples being mannitol, cyclodextrins, poloxamer (i.e., ethylene oxide-propylene oxide block copolymers), methionine, histidine, and mixtures thereof).

The suitable nonpolymeric auxiliaries specifically include:

polyhydric alcohols such as threitol, erythritol, pentaerythritol, arabitol, adonitol, xylitol, sorbitol, mannitol, dulcitol monosaccharides such as arabinose, ribose, xylose, glucose, mannose, galatose, fructose, sorbose, disaccharides such as sucrose, lactose, maltose, trehalose, cellobiose, oligosaccharides such as raffinose, cyclodextrins The resulting solution is applied in the form of individual doses to the carrier substance, which is present in the form of a sheetlike textile structure. The resulting active ingredient layer may then be placed on the backing layer. In one preferred embodiment, however, the carrier substance, which is present in the form of a sheetlike textile structure, is placed on the backing layer before the active ingredient solution is applied, especially when this backing layer is present in the form of an "overpatch" (i.e., when the backing layer is coated on the side facing the active ingredient layer with a water-insoluble, pressure-sensitively adhesive polymer and possesses an area which is larger than the area of the active ingredient layer).

In a further workstep, the resulting assembly is dried, preferably at temperatures below 40° C., more preferably below 30° C., in order to remove the solvents (and also water), preferably down to a desired residual moisture content of 0.5 to 20%, preferably between 1 and 10%. The individually dosed TTS are subsequently packaged.

The examples which follow serve for illustration of the invention, without restricting it.

EXAMPLE 1

FSH in solution in water is mixed with an aqueous phosphate buffer solution (pH 7.0). Added to this solution are cyclodextrin, methionine, poloxamer 188, and meta-cresol for protein stabilization. This solution is then metered with areal precision onto a sheetlike textile structure (nonwoven) which has been placed onto an overpatch.

The table, below shows the composition of the resultant active ingredient layer in the dried state:

| Active ingredient layer | Amount [in mg] | Amount [in %] |
| --- | --- | --- |
| FSH (900 I.U.) | 0.111 | 0.48 |
| cyclodextrin | 20.00 | 86.54 |
| meta-cresol | 0.30 | 1.30 |
| methionine | 0.10 | 0.43 |
| poloxamer 188 | 0.10 | 0.43 |
| sodium monohydrogen phosphate | 1.58 | 6.84 |
| sodium dihydrogen phosphate | 0.92 | 3.98 |
| Total: | 23.111 | 100.00 |

The "cyclodextrin" used in the specific case is hydroxylpropyl-β-cyclodextrin. The material of the pressure-sensitively adhesive layer on the backing layer is a silicone-based pressure-sensitive adhesive with a size of 16.5 cm$^2$, while the layer comprising active ingredient has an area of 5 cm$^2$.

Together with the sheetlike textile structure, the resulting proportions are as follows:

| Active ingredient layer | Amount [in mg] | Amount [in %] |
| --- | --- | --- |
| FSH (900 I.U.) | 0.146 | 0.46 |
| cyclodextrin | 20.00 | 63.2 |
| meta-cresol | 0.30 | 0.95 |
| methionine | 0.10 | 0.3 |
| poloxamer 188 | 0.10 | 0.3 |
| sodium monohydrogen phosphate | 1.58 | 5.0 |
| sodium dihydrogen phosphate | 0.92 | 2.9 |
| sheetlike textile structure | 8.5 | 26.86 |
| Total: | 31.65 | 100.00 |

The active ingredient layer and the protruding edges of the layer of pressure-sensitive adhesive are lined using a siliconized polyester film.

EXAMPLE 2

Specimens as per example 1 are produced, with the difference that the loading with FSH corresponds to 300 I.U./5 cm$^2$, 600 I.U./5 cm$^2$, and 1200 I.U./5 cm$^2$.

EXAMPLE 3

Figure 4:
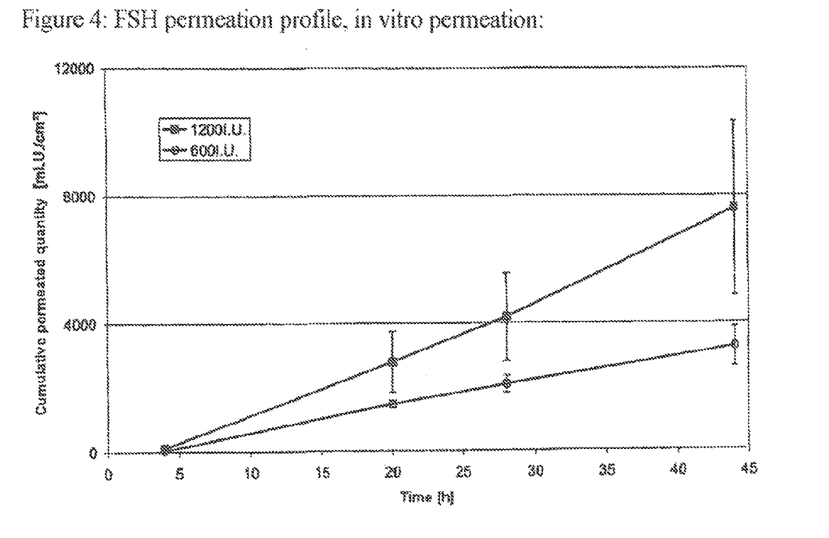
FIG. 4 is a graphical illustration of the effect of the amount of FSH on the in vitro permeation as per Example 2.

Specimens of the transdermal therapeutic systems produced in example 2, with FSH as active ingredient, are investigated for their permeation behaviour through laser-pretreated cow udder skin in a Franz cell. The results of these investigations are shown in FIG. 4.

DESCRIPTION OF THE FIGURES

Figure 1:
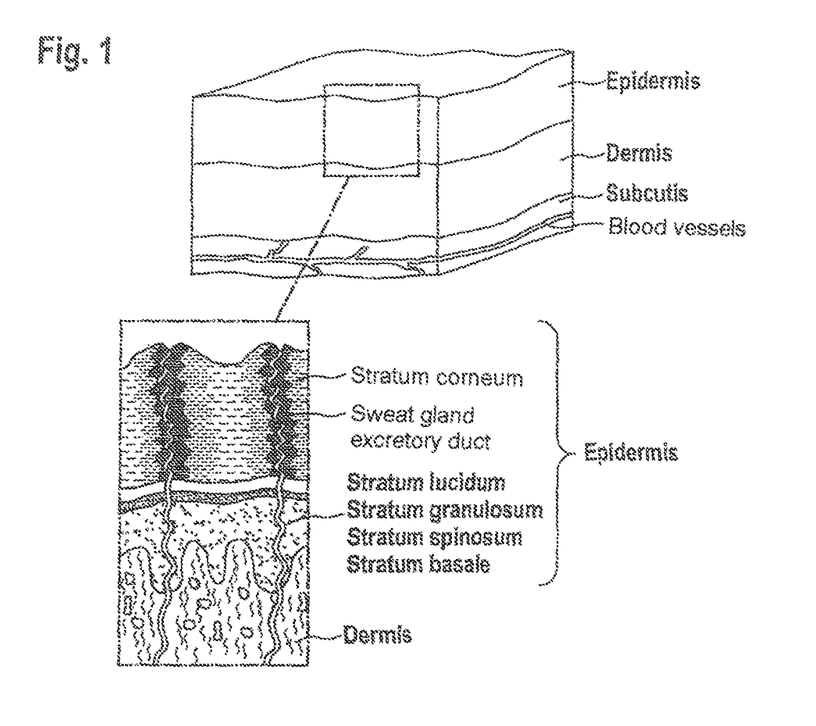
FIG. 1 is a diagrammatic structure of intact, normal skin, with an enlarged section of the outermost layer.
Figure 2:
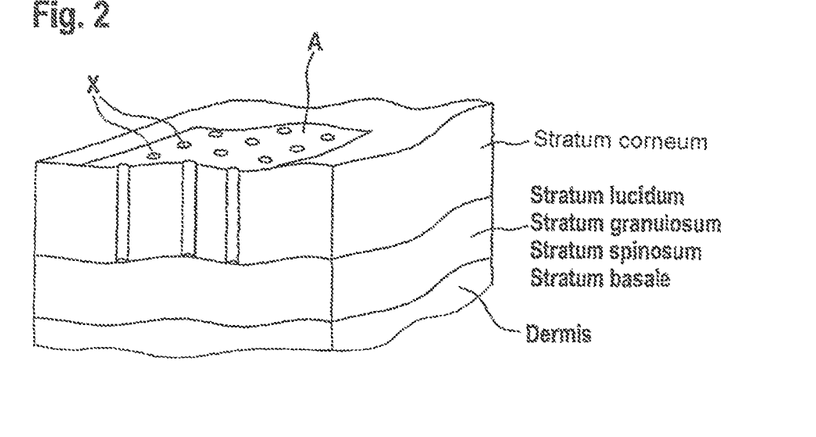
FIG. 2 is a diagrammatic structure of ablatively treated skin.

FIG. 1 shows the diagrammatic structure of intact, normal skin, with an enlarged, section of the outermost layer. Definitions therein are as follows:
E=epidermis
D=dermis
S=subcutis
B=blood vessel
s.c.=stratum corneum
s.l.=stratum lucidum
s.gr.=stratum granulosum
s.sp.=stratum spinosum
s.b.=stratum basale FIG. 2 shows the diagrammatic structure of ablatively treated skin. Here, A denotes the ablatively treated area of skin, and X the areas at which the stratum corneum has been removed.

Figure 3:
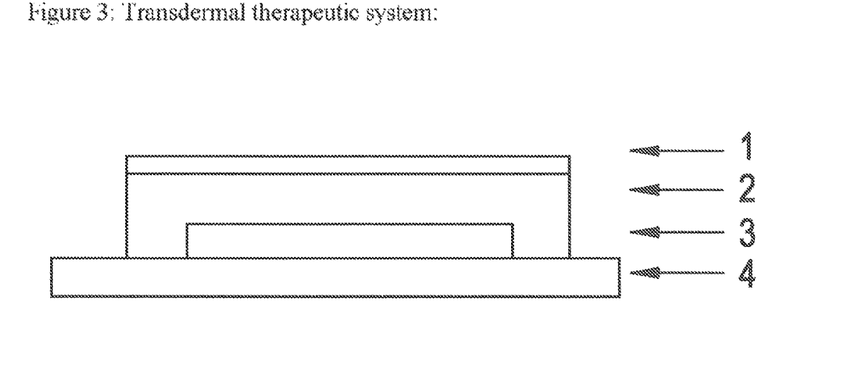
FIG. 3 is a diagrammatic structure of an exemplary inventive transdermal therapeutic system.

FIG. 3 shows the diagrammatic structure of a transdermal therapeutic system as per example 1. Definitions are as follows: 1=backing layer, 2=layer of pressure-sensitive adhesive, 3=active, ingredient layer, 4=protective sheet.

FIG. 4 shows the effect of the amount of FSH on the in vitro permeation as per example 2. The permeation barrier used for the investigations was ablatively treated human skin.

That which is claimed:

1. A method of fertility treatment comprising application of first and second transdermal therapeutic systems, each of the first and second transdermal therapeutic systems comprising (i) a backing layer; (ii) an active ingredient layer; (iii) a pressure-sensitive adhesive and (iv) a removable protective sheet, said method comprising, in a first step, ablatively treating the skin of a female patient by a laser skin ablation technique,
applying the first transdermal therapeutic system with a GnRH agonist as an active ingredient in the active ingredient layer to the skin location treated in the first step and leaving the first transdermal therapeutic system with the GnRH agonist at the skin location treated in the first step for a prolonged time period, the first transdermal therapeutic system delivering the GnRH agonist transdermally to the female patient;
ablatively treating a second skin location on the female patient by a laser skin ablation technique, and
at said second skin location, applying the second transdermal therapeutic system with a follicle-stimulating hormone as an active ingredient in the active ingredient layer, thereby administering follicle stimulating hormone transdermally to bring about the formation of follicles in the female patient.

2. The method as claimed in claim 1, wherein said method further comprises measuring the female patient's endogenous follicle-stimulating hormone level during GnRH agonist delivery to determine if the level is below a target value.

3. The method as claimed in claim 2, wherein the target value is 10 mIU/ml and said method further comprises ablatively treating a third skin location of the female patient by a laser skin ablation technique and applying a third transdermal therapeutic system with a GnRH agonist as active ingredient to the third skin location if the female patient's endogenous follicle-stimulating hormone was above 10 mIU/ml subsequent to administration of the first transdermal therapeutic system.

4. The method as claimed in claim 1, wherein said method further comprises monitoring the formation of follicles in the female patient.

5. The method as claimed in claim 4, wherein said monitoring comprises investigating via ultrasound.

6. The method as claimed in claim 1, wherein said method further comprises removing formed follicles from the female patient, fertilizing the follicles in vitro, and transferring the fertilized follicles into the female patient or a surrogate mother.

7. The method as claimed in claim 1, wherein said laser skin ablation techniques are performed immediately before applying the first and second transdermal therapeutic systems onto the treated first and second skin locations.

8. The method as claimed in claim 1, wherein the first and second transdermal therapeutic systems are applied to the respective ablatively treated first and second skin locations such that the respective active ingredient layers lie directly above the respective ablatively treated first and second skin locations.

9. The method as claimed in claim 1, wherein the active ingredient in said transdermal therapeutic system applied to said second skin location is follicle-stimulating hormone and said method further comprises buffering the active ingredient layer of the second transdermal therapeutic system to a pH of approximately 7.

10. The method as claimed in claim 1, wherein the follicle-stimulating hormone is follitropin.

11. The method as claimed in claim 1, wherein the follicle-stimulating hormone is in the form of a pharmaceutically acceptable salt.

12. The method as claimed in claim 1, wherein the GnRH agonist is selected from leuprolide, buserelin, nafarelin, histrelin, goserelin, deslorelin or triptorelin.

13. The method as claimed in claim 12, wherein the GnRH agonist is triptorelin.

14. The method as claimed in claim 1, wherein said prolonged time period is at least 12 hours.

15. The method as claimed in claim 1, wherein said prolonged time period is 24 to 48 hours.

16. The method as claimed in claim 1, wherein said steps of ablatively treating comprises forming microchannels that do not extend any deeper than down to the skin's dermis.

17. The method as claimed in claim 1, wherein said method further comprises marking the ablatively treated skin with color.

18. The method as claimed in claim 1, wherein the active ingredient layer of either the first or second transdermal therapeutic system comprises at least one substance from the group of nonpolymeric auxiliaries, buffers, stabilizers, and preservatives.

19. The method as claimed in claim 1, wherein the active ingredient layer of either the first or second transdermal therapeutic system has been dried to a residual moisture content of 0.5 to 20%.

20. The method as claimed in claim 19, wherein the active ingredient layer of either the first or second transdermal therapeutic system was applied as a solution onto a carrier substance and the solution comprises an aqueous solution and said method further comprises applying said transdermal therapeutic systems whose active ingredient layers comprising either GnRH agonist or follicle-stimulating hormone have been dried to a residual moisture content of below 5% of the total weight of said layer.

\* \* \* \* \*